United States Patent [19]

Lin

[11] Patent Number: 5,463,166
[45] Date of Patent: Oct. 31, 1995

[54] REACTIVATION OF ALKANE ISOMERIZATION CATALYSTS

[75] Inventor: Fan-Nan Lin, Bartlesville, Okla.

[73] Assignee: Phillips Petroleum Company, Bartlesville, Okla.

[21] Appl. No.: 250,225

[22] Filed: May 27, 1994

[51] Int. Cl.[6] ................ C07C 5/22; B01J 38/10
[52] U.S. Cl. ........................... 585/748; 502/53
[58] Field of Search ............... 502/53; 585/748, 585/742, 734

[56] References Cited

U.S. PATENT DOCUMENTS

| | | |
|---|---|---|
| 2,472,844 | 6/1949 | Mundy . |
| 2,764,528 | 9/1956 | Sweeney ........................ 196/50 |
| 2,908,735 | 10/1959 | Haensel . |
| 2,939,896 | 6/1960 | Myers . |
| 3,389,191 | 6/1968 | Estes ........................ 260/683.74 |
| 4,039,604 | 8/1977 | Myers et al. ................ 260/683.68 |
| 4,045,509 | 8/1977 | Benson, Jr. ........................ 585/742 |
| 4,783,575 | 11/1988 | Schmidt et al. . |
| 4,929,794 | 5/1990 | Schmidt et al. . |

FOREIGN PATENT DOCUMENTS 848198  9/1960  United Kingdom .

*Primary Examiner*—Asok Pal
*Assistant Examiner*—Patrick J. Neill
*Attorney, Agent, or Firm*—K. K. Brandes

[57] ABSTRACT

A process for reactivating a used n-alkane (preferably n-butane) isomerization catalyst comprising platinum, chlorine and a support material comprises contacting the catalyst with flowing hydrogen gas for at least about 1 hour at a temperature of below about 440° F. Preferably, this reactivation process is carried out as an intermittent step in the hydroisomerization of at least one $C_5$–$C_7$ normal alkane (preferably n-butane).

13 Claims, No Drawings

REACTIVATION OF ALKANE ISOMERIZATION CATALYSTS

BACKGROUND OF THE INVENTION

In one aspect, this invention relates to the reactivation of supported platinum- and chlorine-containing catalysts for alkane (in particular, n-butane) isomerization. In another aspect, this invention relates to an alkane (in particular, n-butane) hydroisomerization process comprising the intermittent reactivation of the catalyst used therein.

Supported platinum catalysts are useful for the hydroisomerization of linear (normal) alkanes. These catalysts are subject to deactivation as a result of prolonged usage for a variety of reasons. In the case of n-butane and n-pentane hydroisomerization, for example, dimers and oligomers of these alkanes can be formed as by-products. These by-products tend to accumulate on the catalyst surface and cause a decrease in catalytic isomerization activity. This invention is directed to the removal of these by-products and possibly other catalyst poisons from used isomerization catalysts, thus substantially restoring the activity and prolonging the life of these catalysts.

SUMMARY OF THE INVENTION

It is an object of this invention to treat a used, supported, platinum- and chloride-containing alkane isomerization catalyst so as to substantially enhance its catalytic activity. It is another object of this invention to provide an alkane hydroisomerization process (i.e., isomerization in the presence of hydrogen gas) comprising an intermittent step of treating a partially deactivated, supported, Pt- and Cl-containing isomerization catalyst so as to substantially enhance its catalytic activity. It is a further object of this invention to provide a n-butane hydroisomerization process comprising a intermittent treatment of a partially deactivated Pt/Cl/Al$_2$O$_3$ catalyst so as to substantially enhance its catalytic activity. Other objects and advantages will be apparent from the detailed description and the appended claims.

In accordance with this invention, a partially deactivated alkane isomerization catalyst comprising platinum, chlorine (chemically bound as chloride) and an inorganic support material is contacted with a reducing gas stream consisting essentially of hydrogen for a time period of at least about 1 hour at a temperature of below about 440° F., so as to enhance the isomerization activity of said catalyst.

Also, in accordance with this invention, a process for isomerizing lower alkanes comprises the steps of:

(1) contacting a mixture of (i) a first stream comprising at least one normal alkane (i.e., linear alkane) containing 4–7 carbon atoms per molecule and (ii) a second stream consisting essentially of hydrogen gas with (iii) an isomerization catalyst comprising platinum, chlorine (chemically bound as chloride) and an inorganic support material in a reaction zone at effective alkane isomerization conditions for a prolonged period of time until said catalyst is partially deactivated;

(2) discontinuing the flow of said first stream comprising at least one normal alkane while continuing the flow of said second stream consisting essentially of hydrogen gas in contact with the partially deactivated catalyst formed in step (1), at a temperature of below about 440° F. for a time period of at least about 1 hour; and (3) restarting the flow of said first stream comprising at least one normal alkane while maintaining the flow of said second stream consisting essentially of hydrogen gas, and contacting at effective alkane isomerization conditions said first stream and said second stream with the reactivated catalyst obtained in step (2).

Preferably, steps (2) and (3) are repeated at least once (i.e., once or more than once). Also, preferably, the at least one normal alkane is normal butane (n-butane), and the catalyst comprises (more preferably consists essentially of) platinum, chlorine and alumina (as the support).

DETAILED DESCRIPTION OF THE INVENTION

Any partially deactivated alkane isomerization catalyst (also referred to as "hydroisomerization catalyst" hereinafter) which contains Pt, Cl and a support (preferably alumina) can be used in the processes of this invention. Fresh (unused) alkane isomerization catalysts which catalyze the conversion of C$_4$–C$_7$ alkanes (preferably n-butane) to isoalkanes are well known. They can be prepared by processes described in the patent literature, such as U.S. Pat. Nos. 3,449,264 and 4,014,948. Catalysts for C$_4$, C$_5$ and C$_6$/C$_7$ alkane isomerization are commercially available from various catalyst manufacturers, e.g., from UOP, Inc., Des Plaines, Ill. Generally, these catalysts contain about 0.01–3 (preferably about 0.1–1) weight-% Pt on a suitable inorganic support, preferably alumina. The preferred n-butane isomerization catalysts further contains about 0.5–10 (preferably about 2–6) weight-% Cl. The term "partially deactivated alkane isomerization catalyst", as used herein, refers to an alkane isomerization catalyst which has been employed in a n-alkane hydroisomerization process and has lost a portion (about 10–90%) of its initial isomerization activity (i.e., it has been deactivated to the extent that the catalyst no longer satisfies the desired conversion/selectivity requirement for the n-alkane isomerization process). The weight percentages of Pt and of Cl in the partially deactivated catalyst are essentially the same as those in the fresh catalyst.

In the reactivation (rejuvenation) process of this invention, a partially deactivated, supported, Pt-containing alkane isomerization catalyst is treated with flowing hydrogen gas at a temperature below about 440° F. (generally at about 50°–400° F., preferably at about 80°–350° F., more preferably at about 250°–330° F.), for a time period of at least about 1 hour (preferably about 2 hours to about 10 days, more preferably about 5 hours to about 7 days). The flow rate (gas hourly space velocity) of the reducing gas generally is at about 10–2,000 cc gas/cc catalyst/hour, and preferably is about 50–950 cc/cc/hour. The reducing gas which consists essentially of H$_2$ may contain relatively small amounts of impurities (e.g., about 0.1–10 volume-%) which do not significantly affect the catalyst rejuvenation process, such as N$_2$, CH$_4$, He, and other inert gases.

The above-described catalyst reactivation process is generally carried out as an intermittent step in a continuous alkane (preferably n-butane) hydroisomerization process, i.e., an alkane isomerization process carried out in the presence of hydrogen gas. The basic isomerization reaction conditions in step (1) and also in step (3), are well known and can be varied to achieve the desired conversion in a manner known in the art. Also, the recovery of the product isomer from step (1), and also from step (3), as defined above, can be easily determined by those skilled in the art of alkane isomerization and gas-gas and gas-liquid separations. Isomerization of normal butane (n-butane) to isobutane is the presently preferred reaction step (1), and also step (3). In step (1), the feed alkane and H$_2$ are contacted with a catalyst (generally present in a fixed bed), at a reaction temperature of at least about 200° F., preferably at a temperature of about 200°–450° F. In the preferred case of n-butane isomerization in the presence of $H_2$ gas, the average reaction temperature in the catalyst bed is about 280° F. to about 400° F. The hydrogen-to-alkane molar ratio used in the alkane hydroisomerization process generally is within the range of about 0.01:1 to about 10:1, preferably about 0.05:1 to about 1:1. Generally, the liquid hourly space velocity of the alkane feed stream, i.e., cc of liquid feed per cc of catalyst per hour, is about 0.1 to about 15, and the reaction pressure is within the range of 200 psig to about 1500 psig in the isomerization zone. The gas hourly space velocity of the hydrogen stream is generally about 10–2,000 (preferably about 50–950) cc $H_2$ per cc catalyst per hour (so as to give the above-recited $H_2$:alkane ratio). In order to retard the catalyst deactivation in the isomerization step (1), and also in step (3), about 0.001 to about 1 weight percent chloride is added to the alkane feed, generally in the form of chlorinated hydrocarbon promoters such as carbon tetrachloride, chloroform, ethyl chloride, isopropyl chloride, and the like.

When the catalyst employed in step (1) has lost its activity to the extent that the desired alkane conversion can no longer be attained at the desired reaction temperature, step (2) is carried out, i.e., the flow of the alkane feed is turned off, while the flow of the $H_2$ stream through the isomerization catalyst is maintained, generally at about the same gas hourly space velocity of $H_2$ as in step (1). The temperature in step (2) is generally about the same as in step (1), but may be readjusted upward or downward to maximize the reactivation effect. In the preferred mode of step (2), a reducing gas stream consisting essentially of hydrogen is passed through the partially deactivated isomerization catalyst bed at a temperature of about 50°–400° F. (preferably about 80°–350° F., more preferably about 250°–330° F.) at a GHSV (gas hourly space velocity) of about 10–2,000 cc/cc/hour (more preferably about 50–950 cc/cc/hour), for a time period of about 2 hours to about 10 days (more preferably about 5 hours to about 7 days).

In step (3), the flow of the liquid alkane feed is restarted. If necessary, the temperature in the reactor containing the reactivated isomerization catalyst is adjusted to the desired operating temperature in the isomerization reaction zone, as described for step (1). Step (3), i.e., essentially the alkane isomerization reaction in the presence of the reactivated catalyst obtained in step (2), is carried out for as long as a satisfactory alkane conversion can be achieved, which may be one month or longer (frequently up to 6 months). Then the reactivation step, i.e., step (2), and thereafter step (3) are repeated. These reactivation/isomerization cycles can be repeated as often as feasible, i.e., until finally the catalyst has become deactivated (e.g., by coke deposits) to such a degree that no satisfactory reactivation by hydrogen treatment alone can be achieved.

The following examples are presented to further illustrate the invention and are not to be considered as unduly limiting the scope of the invention.

EXAMPLE I

In this example, lab-scale tests are described to illustrate the process of this invention.

A stainless-steel reactor (having an inner diameter of about 0.75 inch and a height of about 31 inches) was filled with a layer (14 inches high) of Alundum (inert alumina particles having a surface area of 1 $m^2/g$ or less), a layer (10 inches high) of I-8 isomerization catalyst (marketed by UOP; containing about 0.25 weight-% Pt and about 4 weight-% Cl on gamma-alumina; surface area: 165 $m^2/g$) and a bottom layer (12 inches high) of Alundum. The reactor contents were heated to about 300° F., and liquid normal butane was introduced into the reactor at a liquid hourly space velocity of about 4.0 cc/cc/hour, together with hydrogen gas at a flow rate of about 77 cc/minute, so as to provide a 0.25:1 molar ratio of $H_2$ to n-butane. The reaction pressure was about 450 psig. Small amounts (about 200 ppm) of carbon tetrachloride were added to the n-butane feed (so as to retard the deactivation of the catalyst due to Cl loss). The obtained isomerization product (containing isobutane and unconverted n-butane) was analyzed by means of a gas chromatograph. The molar ratio of the formed isobutane to the total butanes (i.e., n-butane and isobutane) in the product was about 0.5:1 at the beginning of the reaction but then dropped to about 0.05:1 after about 10 hours on stream.

Thereafter, the flow of the n-butane feed was interrupted while the $H_2$ gas flow (77 cc/minute) was maintained. Then the reactor cooled down from a peak temperature of about 310° F. to room temperature within a period of about 10 hours in the stream of flowing hydrogen. In a continuation of the test series, the reactor was heated up again, and the hydroisomerization reaction was repeated (with n-butane and $H_2$ as feed streams) employing the reactivated catalyst which had been treated with $H_2$. Approximately the same hydroisomerization conditions as in the previously reported hydroisomerization test were employed. Unexpectedly, the initial molar ratio of isobutane to total butanes in the isomerization product employing the $H_2$-treated, reactivated catalyst was quite high: about 0.54:1 (attained at a reactor temperature of 290° F.). It was concluded that this unexpected activity increase was caused by the previous treatment of the catalyst with flowing $H_2$ (at a temperature starting at 310° F. and then gradually decreasing to room temperature, as described above). The activity of the reactivated catalyst decreased again during this second isomerization run, which lasted about 6 hours, as evidenced by a gradual decrease in the ratio of isobutane to total butanes to about 0.05:1.

Additional reactivation tests with $H_2$ gas showed that subsequent treatment of the catalyst obtained at the end of the second isomerization test run (with flowing $H_2$; no n-butane being present) at about 310° F. again resulted in a molar ratio of about 0.5:1 of isobutane to total butanes in the product of the next isomerization run, whereas treatment of the deactivated catalyst with flowing $H_2$ gas at 390° F. resulted only in a molar isobutane to total butanes ratio of about 0.2:1 in the product of a subsequent isomerization run. These results indicate that the most effective reactivation of an n-butane isomerization catalyst with $H_2$ occurs at a temperature of approximately 300($\pm$20)°F.

EXAMPLE II

This example illustrates the reactivation process of this invention in a commercial n-butane hydroisomerization plant of Phillips 66 Company in Borger, Tex.

A liquid n-butane feed and hydrogen gas were passed through a reactor filled with an I-8 catalyst (described above). The reactor inlet temperature was about 293° F., the liquid n-butane feed rate was about 10,000 barrels per day, and the $H_2$ feed rate was about 5.0 million cubic feet $H_2$ per day. The effective molar ratio of $H_2$ to n-butane was about 0.25:1. The ratio of formed isobutane to total butanes (n- and isobutane) in the isomerization product was 0.57:1.

Thereafter, the flow of the n-butane feed was interrupted, and hydrogen gas was passed through the reactor containing the I-8 catalyst at a starting temperature of about 290° F. for several hours. The reactor and the catalyst contained therein were then allowed to cool to room temperature in the $H_2$ stream. The thus-treated catalyst remained in the reactor at room temperature (under nonflowing $H_2$) for about 1 week. Thereafter, the isomerization process was carried out again, this time employing the $H_2$-treated I-8 catalyst. The n-butane feed rate was again adjusted to about 10,000 barrels per day, and the $H_2$ gas flow rate was about 4.8 million cubic feet per day. It was observed that in order to obtain the desired isobutane to total butane molar ratio of 0.57:1 (as in the previous run), a reactor inlet temperature of only 291° F. was required. Thus, the operating temperature in this plant run employing the $H_2$-treated, reactivated I-8 catalyst was about 2° F. lower than in the prior operation employing an I-8 catalyst which had not been treated with an $H_2$ stream. This lower reaction temperature required to attain a desired isobutane to total butanes ratio (which is a measure of n-butane conversion) indicates that an increase in the catalyst activity due to the previous treatment of the catalyst with a $H_2$ gas stream had been attained.

Reasonable variations, modifications and adaptations for various usages and conditions can be made within the scope of the disclosure and the appended claims, without departing from the scope of this invention.

That which is claimed is:

1. In a process for isomerizing lower alkanes which comprises contacting a mixture of (i) a first stream comprising at least one normal alkane containing 4–7 carbon atoms per molecule and additionally about 0.001–1 weight percent chloride in the form of at least one chlorinated hydrocarbon and (ii) a second stream consisting essentially of hydrogen gas with (iii) an isomerization catalyst consisting essentially of platinum, chlorine and alumina as support material in a reaction zone at effective alkane isomerization conditions comprising a reaction temperature in the range of about 200° F. to about 450° F. for a prolonged period of time until said isomerization catalyst has become a partially deactivated catalyst, the improvement which consists essentially of (a) discontinuing the flow of said first stream comprising at least one normal alkane and at least one chlorinated hydrocarbon while continuing the flow of said second stream consisting essentially of hydrogen gas in contact with said partially deactivated catalyst for a time period of at least about 1 hour at a temperature of about 80°–350° F. so as to obtain a reactivated catalyst, and (b) thereafter restarting the flow of said first stream comprising at least one normal alkane and at least one chlorinated hydrocarbon while maintaining the flow of said second stream consisting essentially of hydrogen gas, and contacting said first stream and said second stream with said reactivated catalyst at said effective isomerization conditions.

2. A process in accordance with claim 1, wherein said at least one normal alkane is n-butane.

3. A process in accordance with claim 1, wherein said catalyst contains about 0.01–3 weight-% platinum and about 0.5–10 weight % chlorine.

4. A process in accordance with claim 1, wherein said catalyst contains about 0.1–1 weight-% platinum and about 2–6 weight-% chlorine.

5. A process in accordance with claim 1, wherein said effective alkane isomerization conditions comprise a hydrogen to alkane molar ratio of about 0.01:1 to about 10:1.

6. A process in accordance with claim 1, wherein said effective alkane isomerization conditions comprise a reaction temperature of about 280°–400° F., a liquid hourly space velocity of said first stream of about 0.1–15 cc/cc catalyst/hour, a gas hourly space velocity of said second stream of about 10–2,000 cc $H_2$/cc catalyst/hour, and a hydrogen to alkane molar ratio of about 0.01:1 to about 10:1.

7. A process in accordance with claim 1, wherein said at least one alkane is n-butane, and said effective alkane isomerization conditions comprise a reaction temperature of about 280°–400° F., a liquid hourly space velocity of said first stream of about 0.1–15 cc/cc catalyst/hour, a gas hourly space velocity of said second stream of about 10–2,000 cc $H_2$/cc catalyst/hour, and a hydrogen to alkane molar ratio of about 0.05:1 to about 1:1.

8. A process in accordance with claim 1, wherein improvement step (a) is carried out at a gas hourly space velocity of said stream consisting essentially of hydrogen of about 10–2,000 cc/cc catalyst/hour, at a temperature of about 250°–330° F., for a time period of about 2 hours to about 10 days.

9. A process in accordance with claim 1, wherein improvement step (a) is carried out at a gas hourly space velocity of said stream consisting essentially of hydrogen of about 50–950 cc $H_2$/cc catalyst/hour, at a temperature of about 280°–320° F., for a time period of about 5 hours to about 7 days.

10. A process in accordance with claim 9, wherein improvement steps (a) and (b) are carried out at least twice.

11. A process in accordance with claim 9, wherein said at least one normal alkane is n-butane.

12. A process in accordance with claim 1, wherein said at least one chlorinated hydrocarbon contained in said first stream is selected from the group consisting of carbon tetrachloride, chloroform, ethyl chloride and isopropyl chloride.

13. A process in accordance with claim 12, wherein said at least one chlorinated hydrocarbon is carbon tetrachloride and said at least one normal alkane contained in said first stream is n-butane.

* * * * *